United States Patent
Chamberlin

(10) Patent No.: US 6,177,574 B1
(45) Date of Patent: Jan. 23, 2001

(54) PREPARATION OF MIXTURES OF BENZOXAZOLYL-STILBENE COMPOUNDS

(75) Inventor: Kim Steven Chamberlin, Kingsport, TN (US)

(73) Assignee: Eastman Chemical Company, Kingsport, TN (US)

(*) Notice: Under 35 U.S.C. 154(b), the term of this patent shall be extended for 0 days.

(21) Appl. No.: 09/517,192

(22) Filed: Mar. 2, 2000

(51) Int. Cl.[7] .................................................. C07D 263/62
(52) U.S. Cl. .............................................................. 548/219
(58) Field of Search ............................................. 548/219

(56) References Cited

U.S. PATENT DOCUMENTS

| | | |
|---|---|---|
| 3,260,715 | 7/1966 | Saunders . |
| 3,407,196 | 10/1968 | Liechti et al. . |
| 3,412,089 | 11/1968 | Ohkawa et al. . |
| 3,546,217 | 12/1970 | Siegrist et al. . |
| 3,577,411 | 5/1971 | Liechti et al. . |
| 3,586,673 | 6/1971 | Bloom et al. . |
| 3,641,044 | 2/1972 | Matter . |
| 3,860,584 | 1/1975 | Meyer . |
| 3,879,356 | 4/1975 | Pacifici . |
| 3,996,210 | 12/1976 | Fleck . |
| 4,197,401 | 4/1980 | Günther et al. . |
| 4,282,355 | 8/1981 | Erckel et al. . |
| 4,310,665 | 1/1982 | Erckel et al. . |
| 4,508,903 | 4/1985 | Heiss . |
| 4,585,875 | 4/1986 | Heiss . |
| 4,921,964 | 5/1990 | Bowers, Jr. et al. . |
| 4,957,932 | 9/1990 | Young et al. . |
| 5,290,941 | 3/1994 | Volante et al. . |
| 5,332,828 | 7/1994 | Wang . |

*Primary Examiner*—Robert W. Ramsuer
*Assistant Examiner*—Sonya N. Wright
(74) *Attorney, Agent, or Firm*—Matthew W. Smith; Harry J. Gwinnell

(57) ABSTRACT

Disclosed is a process for the preparation of a mixture of benzoxazolyl-stilbene compounds by the reaction of unsubstituted 4,4'-bis(benzoxazol-2-yl)stilbene with a substituted o-aminophenol or o-aminonaphthol to obtain a mixture comprising the unsubstituted 4,4'-bis(benzoxazol-2-yl) stilbene and at least one substituted 4,4'-bis(benzoxazol-2-yl)stilbene, 4-naphthoxazol-2-yl-4'-benzoxazol-2-ylstilbene and/or 4,4'-bis(naphthoxazol-2-yl)stilbene. These mixtures are useful as fluorescent brightening agents and light stabilizers for synthetic polymeric materials such as polyesters, polyamide and polyolefin textile materials and shaped articles.

9 Claims, No Drawings

PREPARATION OF MIXTURES OF BENZOXAZOLYL-STILBENE COMPOUNDS

FIELD OF THE INVENTION

The present invention is pertains to a process for the preparation of a mixture of benzoxazolyl-stilbene compounds. More specifically, this invention pertains to a process for preparing a mixture of 4,4'-bis(benzoxazol-2-yl) stilbene compounds by the reaction of unsubstituted 4,4'-bis(benzoxazol-2-yl)stilbene with a substituted o-aminophenol to obtain a mixture comprising the unsubstituted 4,4'-bis(benzoxazol-2-yl)stilbene and at least one substituted 4,4'-bis(benzoxazol-2-yl)stilbene, 4-naphthoxazol-2-yl-4'-benzoxazol-2-ylstilbene and/or 4,4'-bis(naphthoxazol-2-yl)stilbene. These mixtures are useful as fluorescent brightening agents and light stabilizers for synthetic polymeric materials such as polyesters, polyamide and polyolefin textile materials and shaped articles.

BACKGROUND OF THE INVENTION

Optical brighteners compensate for the yellow cast produced by light or heat degradation of the polymer over time. Typical optical brighteners fluoresce upon irradiation with ultraviolet light emitting visible light, typically bluish in hue, replacing the light that would have been lost and thereby enhancing brightness. Optical brighteners mask undesirable tints, such as yellow tint from recycled products, and/or modify the fluorescent nature of certain color imparting pigments.

4,4'-Bis(benzoxazol-2-yl)stilbene has been used extensively as an optical brightener for synthetic polymeric materials such as polyesters, e.g., poly(ethylene terephthalate), and polyamides, e.g., nylon 6,6. 4,4'-Bis (benzoxazol-2-yl)stilbene, also having the chemical name 2,2'-(1,2-ethenediyl di 4,1-phenylene)bis benzoxazole, typically is incorporated into such synthetic polymers by the technique known as "mass brightening" wherein the optical brightener (or whitener) is added to a melt of the polymer prior to its conversion into a shaped article such as a fiber or filament suitable for use in the textile industry. Mixtures of unsubstituted and substituted 4,4'-bis(benzoxazol-2-yl) stilbene compounds are more effective than is the unsubstituted compound for certain uses, e.g., for topical application to textile materials such as fibers, filaments and fabrics prepared from polyesters and in the manufacture of photographic paper wherein the lower melting point of the mixture is advantageous.

A particularly efficient method for the preparation of unsubstituted 4,4'-bis(benzoxazol-2-yl)stilbene comprises the steps of (1) reacting an alkyl p-toluate with o-aminophenol to produce 2-(p-tolyl)benzoxazole and (2) heating 2-(p-tolyl)benzoxazole with sulfur to dehydrodimeize the 2-(p-tolyl)benzoxazole and produce 4,4'-bis (benzoxazol-2-yl)stilbene. Although it is eminently suited for the synthesis of unsubstituted 4,4'-bis(benzoxazol-2-yl) stilbene, the toluate ester method is not especially useful for preparing substituted 4,4'-bis(benzoxazol-2-yl)stilbene, e.g., compounds wherein one or both of the benzoxazole rings are substituted with an alkyl group, or mixture of such compounds with unsubstituted 4,4'-bis(benzoxazol-2-yl) stilbene. Such substituted compounds and mixtures may be prepared by first synthesizing 4,4'-stilbenedicarboxylic acid or an ester or diester thereof and reacting the 4,4'-stilbenedicarboxylic acid or ester with a mixture comprising unsubstituted o-aminophenol and at least one substituted o-aminophenol such as 2-amino-4-methylphenol. The product consists of a mixture unsubstituted 4,4'-bis(benzoxazol-2-yl)stilbene, mono-substituted 4,4'-bis(benzoxazol-2-yl) stilbene, i.e., 4-(5-methylbenzoxazol-2-yl)-4'-(benzoxazol-2-yl)stilbene, and disubstituted 4,4'-bis(benzoxazol-2-yl) stilbene, i.e., 4,4'-bis(5-methylbenzoxazol-2-yl)stilbene.

The processes described in U.S. Pat. No. 4,921,964 are typical of the known processes for the preparation of mixtures of 4,4'-bis(benzoxazol-2-yl)stilbene compounds. That patent describes the preparation of unsubstituted 4,4'-bis (benzoxazol-2-yl)stilbene as well as the aforesaid mixture of 4,4'-bis(benzoxazol-2-yl)stilbene, 4-(5-methylbenzoxazol-2-yl)-4'-(benzoxazol-2-yl)stilbene, and 4,4'-bis(5-methylbenzoxazol-2-yl)stilbene, by reacting dimethyl 4,4'-stilbenedicarboxylate with o-aminophenol or a mixture of o-aminophenol and 2-amino-4-methylphenol. The reaction typically is carried out at a temperature of about 200 to 250° C. in the presence of tin or titanium catalyst.

BRIEF SUMMARY OF THE INVENTION

A process now has been developed for the preparation of a mixture of 4,4'-bis(benzoxazol-2-yl)stilbene compounds by the reaction of 4,4'-bis(benzoxazol-2-yl)stilbene with certain o-aminophenols and/or o-aminonaphthols. The mixture obtained from the process comprises unsubstituted 4,4'-bis(benzoxazol-2-yl)stilbene and at least one other compound selected from a substituted 4,4'-bis(benzoxazol-2-yl) stilbene wherein the o-phenylene residue of one or both benzoxazol-2-yl is substituted or the o-phenylene residue of one or both benzoxazol-2-yl has been replaced with an o-naphthylene residue, e.g., 1,2- or 2,3-naphthylene. The present invention provides a process for preparing a mixture of at least two compounds having the general formula:

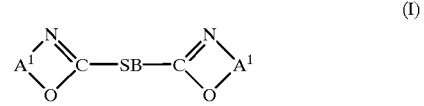

(I)

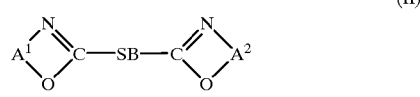

(II)

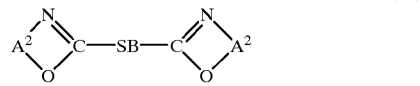

(III)

which comprises the reaction of 4,4'-bis(benzoxazol-2-yl) stilbene having the general formula:

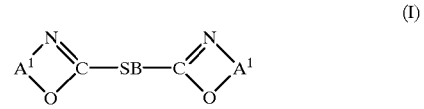

(I)

with a compound having the general formula:

(IV)

at a temperature of at least 200° C. in the presence of an inert, i.e., non-reactive, solvent; wherein $A^1$ is o-phenylene; $A^2$ is selected from o-napthylene or substituted o-phenylene;

and SB is 4,4'-stilbenediyl. The process may be used to produce mixtures comprising two or more compounds without the need for preparing 4,4'-stilbenedicarboxylic acid or ester. The reaction may be facilitated by carrying out the process in the presence of a catalyst, e.g., a transition metal Lewis acid such as an inorganic or organometallic compound of titanium, tin, antimony, zirconium and the like.

DETAILED DESCRIPTION

Reactant (IV) may be one or more compounds selected from o-aminonapthols or ring-substituted o-aminophenols wherein the substituents are selected from alkyl, cyano, alkylsulfonyl, halogen and aryl. The o-aminophenol ring may be substituted with two substitutents, e.g., two methyl groups, but typically is substituted with one group. Examples of the alkyl groups include alkyl containing up to about 12 carbon atoms such as methyl, ethyl, butyl, tertiary butyl, octyl, tertiary octyl (1,1,3,3-tetramethylbutyl) and the like. The alkylsulfonyl groups may contain up to about six carbon atoms, e.g., methylsulfonyl, butylsulfonyl and hexylsulfonyl. Chloro and bromo are examples of the halogen substituents. Carbocyclic aryl such as phenyl and phenyl substituted with lower (1–4 carbon atoms) alkyl, lower alkoxy and halogen represent examples of the aryl groups which may be present on the substituted o-aminophenol reactants. The substituted o-aminophenol reactant preferably is an alkyl-substituted o-aminophenol, especially 2-amino-4-methylphenol.

The process of the present invention is preferably carried out using a a broad range of Reactant (IV):Reactant (I) mole ratios, depending, for example, upon the particular Reactant (IV) used, and product mixture which is desired, the reaction conditions and/or other process variable. Normally, the Reactant (IV):Reactant (I) molar ratio is in the range of from about 0.25:1 to 5:1, preferably from about 0.5:1 to 2:1. The mole ratio of compounds (I), (II) and, optionally, (III) produced by my novel process typically is a (I):(II):(III) mole ratio in the range of about 0.1–10:1:0–1 and preferably is in the range of 6–1:1:0.25–0.5.

The process normally is carried out at a temperature of at least about 200° C., e.g., about 200 to 300° C., and preferably at a temperature in the range of about 220 to 260° C. Pressure is not an important feature of the present process and, thus, the process may be carried out at pressures moderately above or below ambient pressure. Elevated pressure, e.g., pressures up to about 6 bar absolute, may be used to achieve a process temperature of at least 200° C. when using an inert solvent which has a normal boiling point below 200° C.

Inert (non-reactive), organic solvents which may be used in the process preferably are those organic solvents that boil above about 200° C. and are substantially unreactive toward reactants and any catalyst used and products produced. The organic solvent preferably solubilizes impurities such that no further purification is needed after simple filtration and washing. Specific examples of suitable organic solvents include chloronaphthalene, methylnaphthalene, dimethylnaphthalene, chloronaphthalene, naphthalene, biphenyl, biphenyl ether, diphenyl ether, diphenyl ethane, alkyl substituted diphenylethanes and any mixture of two or more thereof. The amount of solvent is not important and can be varied over a wide range. Normally, the amount of a solvent employed provides a solvent:reactant, i.e., reactants (I) and (IV), weight ratio in the range of about 10:1 to 2:1.

The reaction of the present process will proceed without the aid of a catalyst. However, it is more efficient to conduct the reaction in the presence of a catalyst such as a transition metal Lewis acid. Examples of such catalysts include the halides, oxides and organo derivatives of titanium, antimony, tin and zirconium. Especially preferred among the titanium compounds are the titanium tetraalkoxides, especially those in which the alkyl moieties contain 1 to about 8 carbon atoms, such as titanium tetraisopropoxide. For example, catalysts concentrations of 2000 to 8000 parts per million by weight (ppmw) Ti metal, based on the total weight of reactants (I) and (IV), are preferred for the titanium catalysts.

An especially preferred embodiment of the present process is represented by the preparation of a mixture of 4,4'-bis(benzoxazol-2-yl)stilbene, 4-(5-methylbenzoxazol-2-yl)-4'-(benzoxazol-2-yl)stilbene, and 4,4'-bis(5-methylbenzoxazol-2-yl)stilbene, by reacting 4,4'-bis(benzoxazol-2-yl)stilbene with 2-amino-4-methylphenol in the presence of an inert organic solvent and a titanium tetraalkoxide catalyst.

The process provided by my invention is further illustrated by the following examples. Reactant (I) used in the examples is produced and sold by Eastman Chemical Company under the tradename EASTOBRITE OB-1 optical brightener ("OB-1"). The compositions of the products obtained in the examples were determined by liquid chromatography and are given as area percentages. Structure identifications were made by liquid chromatography/mass spectroscopy.

EXAMPLE 1

OB-1 (5.18 g, 0.0125 mole), 2-amino-4-methylphenol (1.54 g, 0.0125 mole), and titanium tetraisopropoxide (0.05 g) were refluxed (241–243° C.) overnight in 50 mL of 1-methylnaphthalene. The mixture was cooled to ambient temperature. The product was collected by filtration, washed with methanol (50 mL) and dried to yield 4.16 g of product comprising 62.9% 4,4'-bis(benzoxazol-2-yl)stilbene, 31.7% 4-(5-methylbenzoxazol-2-yl)-4'-(benzoxazol-2-yl)stilbene, and 3.5% 4,4'-bis(5-methylbenzoxazol-2-yl)stilbene.

EXAMPLE 2

OB-1 (5.18 g, 0.0125 moles), 2-amino-4-methylphenol (3.08 g, 0.025 moles), and titanium tetraisopropoxide (0.05 g) were refluxed overnight in 50 mL of 1-methylnaphthalene. The mixture was cooled to ambient temperature. The product was collected by filtration, washed with methanol (50 mL) and dried to yield 5.21 g of product comprising 51.0% 4,4'-bis(benzoxazol-2-yl)stilbene, 39.7% 4-(5-methylbenzoxazol-2-yl)-4'-(benzoxazol-2-yl)stilbene, and 13.2% 4,4'-(5-methylbenzoxazol-2-yl)stilbene.

EXAMPLE 3

OB-1 (5.18 g, 0.0125 moles), 2-amino-4-methylphenol (4.62 g, 0.0375 moles), and titanium tetraisopropoxide (0.05 g) were refluxed overnight in 50 mL of 1-methylnaphthalene. The mixture was cooled to ambient temperature. The product was collected by filtration, washed with methanol (50 mL) and dried to yield 5.28 g of product comprising 23.7% 4,4'-bis(benzoxazol-2-yl)stilbene, 49.5% 4-(5-methylbenzoxazol-2-yl)-4'-(benzoxazol-2-yl)stilbene, and 26.9% 4,4'-bis(5-methylbenzoxazol-2-yl)stilbene.

EXAMPLE 4

OB-1 (5.18 g, 0.0125 moles), 2-amino 4-chlorophenol (3.59 g, 0.025 moles), and titanium tetraisopropoxide (0.05 g) were refluxed overnight in 50 mL of 1-methylnaphthalene. The mixture was cooled to ambient temperature. The product was collected by filtration, washed with methanol (50 mL) and dried to obtain 5.63 g of product comprising 67.1% 4,4'-bis(benzoxazol-2-yl)stilbene, 29.8% 4-(5-chlorobenzoxazol-2-yl)-4'-(benzoxazol-2-yl)stilbene, and 32.6% 4,4'-bis(5-chlorobenzoxazol-2-yl)stilbene.

EXAMPLE 5

OB-1 (5.18 g, 0.0125 moles), 2-amino 4-tert-butylphenol (4.13 g, 0.025 moles), and titanium tetraisopropoxide (0.05 g) were refluxed overnight in 50 mL of 1-methylnaphthalene. The mixture was cooled to ambient temperature. The product was collected by filtration, washed with methanol (50 mL) and dried to yield 4.64 g of product comprising 40.0% 4,4'-bis(benzoxazol-2-yl)stilbene, 49.1% 4-(5-tert-butylbenzoxazol-2-yl)-4'-(benzoxazol-2-yl) stilbene, and 11.0% 4,4'-bis(5-tert-butylbenzoxazol-2-yl) stilbene.

EXAMPLES 6

OB-1 (5.18 g, 0.0125 moles), 2-amino-3-methylphenol (3.08 g, 0.025 moles), and titanium tetraisopropoxide (0.05 g) were refluxed overnight in 50 mL of 1-methylnaphthalene. The mixture was cooled to ambient temperature. The product was collected by filtration, washed with methanol (50 mL) and dried to yield 3.31 g of product comprising 14% 4,4'-bis(benzoxazol-2-yl)stilbene, 47.1% 4-(4-methylbenzoxazol-2-yl)-4'-(benzoxazol-2-yl)stilbene, and 39.3% 4,4'-bis(4-methylbenzoxazol-2-yl)stilbene.

EXAMPLE 7

OB-1 (5.18 g, 0.0125 moles) and 2-amino-4-methylphenol (3.08 g, 0.025 moles) were refluxed overnight in 50 mL of 1-methylnaphthalene. The mixture was cooled to ambient temperature. The product was collected by filtration, washed with methanol (50 mL) and dried to yield 3.76 g of product comprising 89.5% 4,4'-bis(benzoxazol-2-yl)stilbene and 10.5% 4-(5-methylbenzoxazol-2-yl)4'-(benzoxazol-2-yl)stilbene.

EXAMPLE 8

OB-1 (5.18 g, 0.0125 moles) and 2-amino-4-methylphenol (4.62 g, 0.0375 moles) were refluxed overnight in 50 mL of 1-methylnaphthalene. The mixture was cooled to ambient temperature. The product was collected by filtration, washed with methanol (50 mL) and dried to yield 3.80 g of product comprising 86.0% 4,4'-bis (benzoxazol-2-yl)stilbene and 14.0% 4-(5-methylbenzoxazol-2-yl)-4'-(benzoxazol-2-yl)stilbene.

EXAMPLE 9

OB-1 (5.18 g, 0.0125 moles) and 2-amino 4-chlorophenol (3.59 g, 0.025 moles) were refluxed overnight in 50 mL of 1-methylnaphthalene. The mixture was cooled to ambient temperature. The product was collected by filtration, washed with methanol (50 mL) and dried to yield 4.74 g of product comprising 89.4% 4,4'-bis(benzoxazol-2-yl)stilbene and 10.6% 4-(5-chlorobenzoxazol-2-yl)-4'-(benzoxazol-2-yl) stilbene.

EXAMPLE 10

OB-1 (5.18 g, 0.0125 moles) and 2-amino 4-tert-butylphenol (4.13 g, 0.025 moles) were refluxed overnight in 50 mL of 1-methylnaphthalene. The mixture was cooled to ambient temperature. The product was collected by filtration, washed with methanol (50 mL) and dried to yield 4.00 g of product comprising 91.44% 4,4'-bis(benzoxazol-2-yl)stilbene and 10.6% 4-(5-tert-butylbenzoxazol-2-yl)-4'-(benzoxazol-2-yl)stilbene.

EXAMPLE 11

OB-1 (9.0 g, 0.0217 moles) and 2-amino 4-(1,1,3,3-tetramethylbutyl)phenol (9.0 g, 0.0406 moles) were heated to 250° C. and held at 250° C. overnight. The mixture was cooled to ambient temperature and diluted with 1-methylnaphthalene. The product was collected by filtration, washed with methanol (50 mL) and dried to yield 4.64 g of product comprising 45.4% 4,4'-bis[benzoxazol-2-yl]stilbene, 49.5% 4-[5-(1,1,3,3-tetramethylbutyl) benzoxazol-2-yl]-4'-[benzoxazol-2-yl]stilbene, and 5.1% 4,4'-bis[5-(1,1,3,3-tetramethylbutyl)benzoxazol-2-yl] stilbene.

The invention has been described in detail with particular reference to preferred embodiments thereof, but it will be understood that variations and modifications can be effected within the spirit and scope of the invention.

I claim:

1. Process for preparing a mixture of at least two compounds having the general formula:

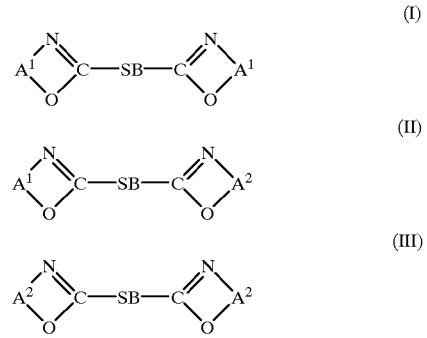

which comprises reacting 4,4'-bis(benzoxazol-2-yl)stilbene having the general formula:

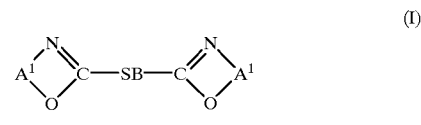

with a compound having the formula:

at a temperature of at least 200° C. in the presence of an inert solvent; wherein $A^1$ is o-phenylene; $A^2$ is selected from o-napthylene and substituted o-phenylene; and SB is 4,4'-stilbenediyl.

2. Process according to claim 1 wherein $A^2$ is o-naphthylene or o-phenylene substituted with alkyl, cyano, alkylsulfonyl, halogen or aryl.

3. Process according to claim 1 wherein the process is carried out at a temperature of about 220 to 260° C., the Reactant (IV):Reactant (I) molar ratio is in the range of from about 0.25:1 to 5:1, and $A^2$ is o-naphthylene or o-phenylene substituted with alkyl of up to about 12 carbon atoms, cyano, alkylsulfonyl of up to about 6 carbon atoms, chloro, bromo, or phenyl.

4. Process according to claim 3 wherein the process is carried out in the presence of a transition metal Lewis acid catalyst.

5. Process according to claim 3 wherein the process is carried out in the presence of a titanium, antimony, tin or zirconium Lewis acid catalyst.

6. Process according to claim 1 wherein the process is carried out at a temperature of about 220 to 260° C. in the presence of a titanium tetraalkoxide catalyst, the Reactant (IV):Reactant (I) molar ratio is in the range of from about 0.5:1 to 2:1, and $A^2$ is o-phenylene substituted with alkyl of up to about 12 carbon atoms, chloro, or bromo.

7. Process according to claim 1 wherein the process is carried out in the presence of an inert solvent selected from chloronaphthalene, methylnaphthalene, dimethylnaphthalene, chloronaphthalene, naphthalene, biphenyl, biphenyl ether, diphenyl ether, and a mixture of any two or more thereof.

8. Process for the preparation of a mixture of 4,4'-bis(benzoxazol-2-yl)stilbene, 4-(5-methylbenzoxazol-2-yl)-4'-(benzoxazol-2-yl)stilbene, and 4,4'-bis(5-methylbenzoxazol-2-yl)stilbene which comprises reacting 4,4'-bis(benzoxazol-2-yl)stilbene with 2-amino-4-methylphenol at a temperature of at least 200° C. in the presence of an inert organic solvent and a titanium tetraalkoxide catalyst.

9. Process according to claim 8 wherein the process is carried out at a temperature of about 220 to 260° C. and the molar ratio of 2-amino-4-methylphenol:4,4'-bis(benzoxazol-2-yl)stilbene is about 0.5:1 to 2:1.

* * * * *